US00PP30290P2

(12) United States Plant Patent
van den Top

(10) Patent No.: US PP30,290 P2
(45) Date of Patent: Mar. 12, 2019

(54) ***HOSTA* PLANT NAMED 'B200'**

(50) Latin Name: *Hosta hybrida*
Varietal Denomination: B200

(71) Applicant: Hendrik Jan van den Top, Barneveld (NL)

(72) Inventor: Hendrik Jan van den Top, Barneveld (NL)

( * ) Notice: Subject to any disclaimer, the term of this patent is extended or adjusted under 35 U.S.C. 154(b) by 0 days.

(21) Appl. No.: 15/732,438

(22) Filed: Nov. 13, 2017

(51) Int. Cl.
*A01H 5/12* (2018.01)

(52) U.S. Cl.
USPC ..... Plt./353

(58) Field of Classification Search
USPC ..... Plt./353
CPC ... A01H 5/12; A01H 5/02; A01H 5/00; A01H 5/0272; A01H 6/56
See application file for complete search history.

*Primary Examiner* — June Hwu
(74) *Attorney, Agent, or Firm* — Penny J. Aguirre

(57) ABSTRACT

A new cultivar of *Hosta* named 'B200' that is characterized by its variegated foliage with yellow-gold centers in color and green margins with some streaks of green into the centers, its leaf margins that are ruffled, its vigorous growth habit, and its high tolerance to sun scorch.

2 Drawing Sheets

Botanical classification: *Hosta hybrida.*
Cultivar designation: 'B200'.

BACKGROUND OF THE INVENTION

The present invention relates to a new and distinct cultivar of *Hosta*, botanically of hybrid origin and known as a *Hosta* 'B200' and is hereinafter referred to by its cultivar name 'B200'.

The new cultivar was discovered by the Inventor in May of 2012 as a naturally-occuring chimeral mutation of *Hosta* 'Dancing Queen' (not patented) that was growing in a container outdoors in Barneveld, The Netherlands.

Asexual propagation of the new cultivar was first accomplished by division by the Inventor in Barneveld, The Netherlands in 2013. Asexual propagation of the new cultivar by division and tissue culture using meristematic tissue has shown that the unique features are stable and reproduced true to type in successive generations.

SUMMARY OF THE INVENTION

The following traits have been repeatedly observed and represent the characteristics of the new cultivar. These attributes in combination distinguish 'B200' as a new and unique cultivar of *Hosta.*

1. 'B200' exhibits variegated foliage with yellow-gold centers in color and green margins with some streaks of green into the centers.
2. 'B200' exhibits leaf margins that are ruffled.
3. 'B200' exhibits a vigourous growth habit.
4. 'B200' exhibits a high tolerance to sun scorch.

The parent plant, 'Dancing Queen', differs from 'B200' in having a shorter plant height and in lacking variegated foliage. 'B200' can be most closely compared to the *Hosta* cultivars 'On Stage' (not patented) and 'One Last Dance' (U.S. Plant patent application Ser. No. 15/530,300). 'On Stage' is similar to 'B200' in having a similar leaf variegation with yellow-gold centers and green margins. 'On Stage' differs from 'B200' in having a shorter plant height, leaf margins that are not ruffled, and in having a more upright plant habit. 'One Last Dance' is similar to 'B200' in being a chimeral mutation of 'Dancing Queen'. 'One Last Dance' differs from 'B200' in having the reverse leaf variegation pattern by exhibiting green centers and yellow-gold margins.

BRIEF DESCRIPTION OF THE DRAWINGS

The accompanying colored photographs illustrate the overall appearance and distinct characteristics of the new *Hosta*. The photographs were taken of 2 year-old plants as grown outdoors in a 27-cm container in Barneveld, The Netherlands.

Figure 1:
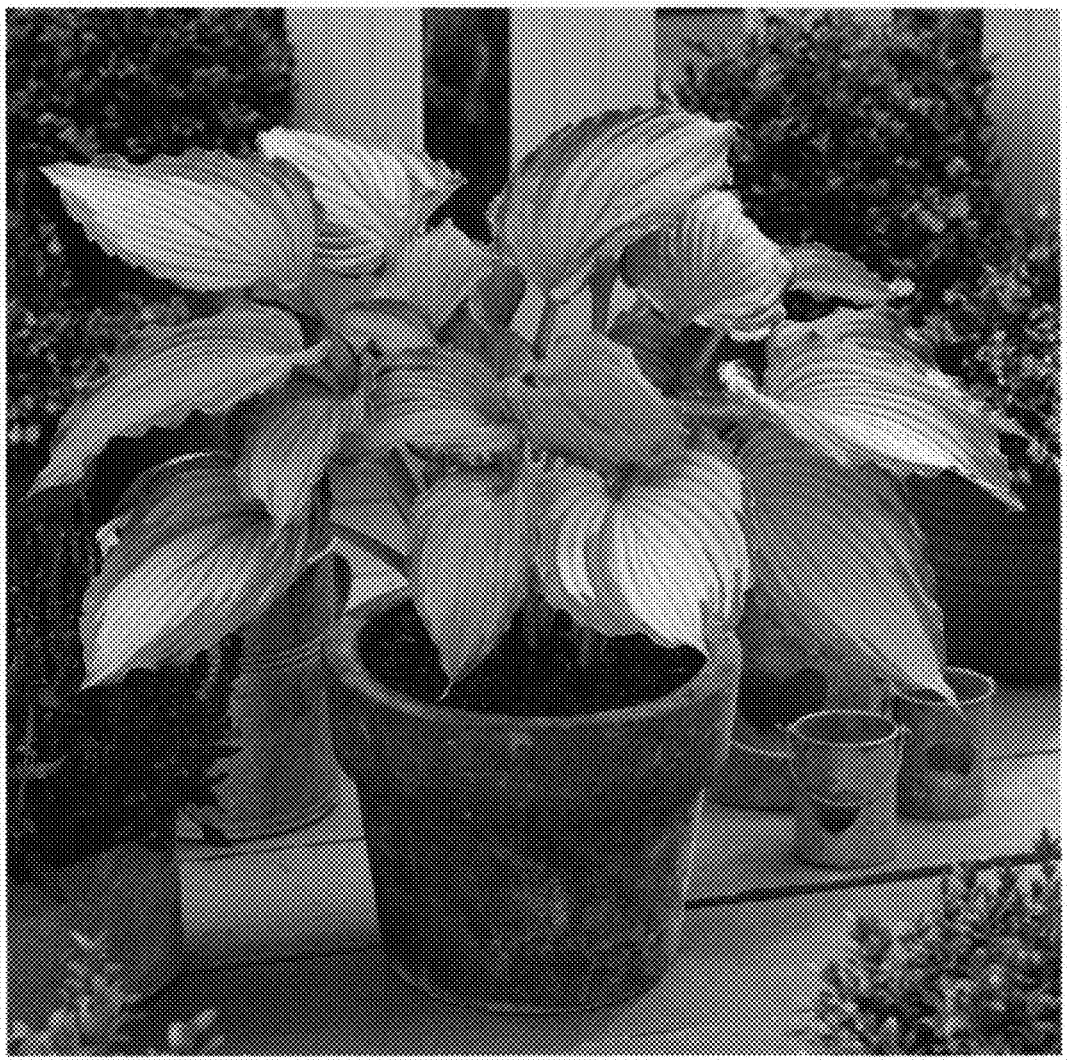
FIG. 1 provides an overall view of the plant of 'B200'.
Figure 2:
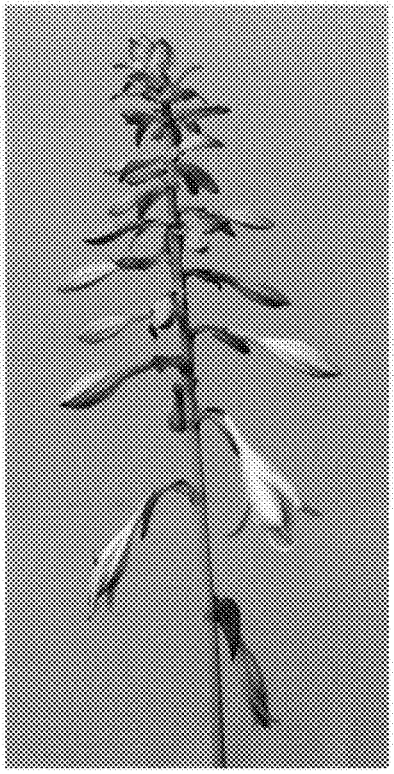

The photograph in FIG. 2 provides a close-up view of an inflorecence of 'B200'.

Figure 3:
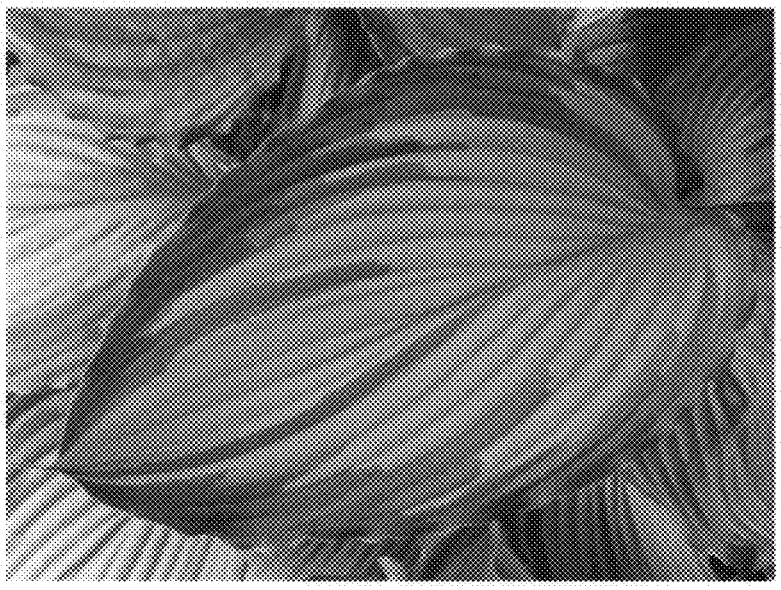

FIG. 3 provides a close-up view of a leaf of 'B200'.

The colors in the photographs are as close as possible with the photographic and printing technology utilized and the color values cited in the Detailed Botanical Description accurately describe the colors of the new *Hosta.*

DETAILED BOTANICAL DESCRIPTION OF THE PLANT

The following is a detailed description of 2 year-old plants as grown outdoors in a 27-cm container in Barneveld, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—July in The Netherlands.

*Plant type*.—Herbaceous perennial.

*Plant habit*.—Broad spreading to upright, compact.

*Height and spread*.—An average of 40 to 50 cm in height (to top of foliage) and 60 cm cm in width as a 2 year-old plant in the landscape.

*Cold hardiness*.—At least in U.S.D.A. Zone 4.

*Diseases*.—No susceptibility or resistance to diseases has been observed.

*Environmental conditions*.—Highly tolerance to sun scorch.

*Root description*.—Freely branched, fleshy, 162D in color.

*Root development*.—About 20 weeks to produce a plant in an 11 cm container.

*Propagation*.—Tissue culture is the preferred, division is also possible.

*Growth rate*.—Vigorous.

Foliage description:

*Leaf shape*.—Ovate to narrow cordate.

*Leaf division*.—Simple.

*Leaf base*.—Obtuse to cordate.

*Leaf apex*.—Apiculate.

*Leaf venation*.—Camptodrome pattern, upper surface color; 150C, margins and stripes 137B and N144C, lower surface color; 139D.

*Leaf margins*.—Entire and ruffled.

*Leaf attachment*.—Petiolate.

*Leaf aspect*.—Slightly concave to downward.

*Leaf arrangement*.—Alternate, in basal rosettes.

*Leaf surface*.—Upper and lower surface is glabrous and slighty glossy, under side veins are furrowed.

*Leaf orientation*.—Held nearly upright to outward and downward on upright petioles.

*Leaf color*.—Young upper surface; between 144D and N144D, margined and slightly axially striped 137C to 137D and 144B, young lower surface; N144D, margined and slightly axially striped 146A and 146D, mature upper surface; 150C, margined and slightly axially striped 137B and N144C, mature lower surface; between 150B and 151D, margined and slightly axially striped 146B and 144C.

*Leaf size*.—Average of 25.6 cm in length and 16.5 cm in width.

*Leaf quantity*.—Average of 7 per basal rosette.

*Petioles*.—Average of 20.3 cm in length, average of 1.5 cm in diameter, both surfaces are glabrous and smooth, v-shaped, strong, color upper surface; 144B, margins 143A to 143B, color of lower surface; 145A to 145C, margins 147B.

Flower description:

*Inflorescence type*.—Terminal racemes of single bell-shaped flowers.

*Inflorescence size*.—34.8 cm in height, 13 cm in width.

*Lastingness of inflorescence*.—About 4 weeks from first opening bloom to fading of last opening bloom, individual blooms last up to 5 days, self cleaning.

*Flower type*.—Campanulate, single.

*Flower/inflorescence number*.—Average of 6 inflorescences per plant, 46 flowers per inflorescence.

*Flower fragrance*.—None.

*Flower aspect*.—Drooping.

*Flower buds*.—Average of 3.6 cm in length, 9 mm in diameter, oblanceolate in shape, smooth, glabrous and glossy surface, color; N88D, striped 85D and N155A, base 85D.

*Flower size*.—Average of 7 cm in depth, 4.1 cm in diameter.

*Peduncles*.—An average of 93.1 cm in length, 5 mm in diameter, held in an average angle of 75°, strong, smooth and glabrous surface, 145A in color.

*Pedicels*.—An average of 1.6 cm in length, 2 mm in diameter, held in an average angle of 40°, strong, smooth and glabrous surface, 148A to 148B in color.

*Calyx*.—None present, repals form a corolla described under flower shape.

*Tepals*.—6, rotate, fused into campanulate shape, upper 40% of the tepals are free, glabrous and dull surfaces, entire margins, acute apex, 6.8 cm in length, outer tepal 1.2 cm in width, inner tepal 1.4 cm in width, color of outer and inner tepals; when opening and fully open outer surface 85B and 85C with margins and base N155B, when opening and fully open inner surface 85C and 85D, both surfaces fading to N88D.

*Floral bracts*.—1 at the base of each pedicel, ovate to lanceolate in shape, apiculate apex, truncate base, both surfaces are smooth and glabrous, average of 2.2 cm in length and 1.3 cm in width, color of both surfaces 145A and tinged with N186B.

Reproductive organs:

*Gynoecium*.—Pistil; 1, 7.1 cm in length, style; 7 cm in length, 145C to 145D, stigma; crested in shape, 1 mm in length and diameter, 145D in color, ovary is 144C in color.

*Androecium*.—Stamens; 6, filament; curled, 157C to 157D in color, 6.4 cm in length, anthers; 3 mm in length, dorsifixed, oblong in shape, N187A in color, pollen is abundant and 14A in color.

*Fruit/seed*.—Production of seed capsules has not been not observed to date.

It is claimed:

1. A new and distinct cultivar of *Hosta* plant named 'B200' as herein illustrated and described.

* * * * *